(12) United States Patent
Takahashi

(10) Patent No.: US 11,273,111 B2
(45) Date of Patent: Mar. 15, 2022

(54) ORAL COMPOSITION

(71) Applicant: KAO CORPORATION, Tokyo (JP)

(72) Inventor: Yuko Takahashi, Taito-ku (JP)

(73) Assignee: KAO CORPORATION, Tokyo (JP)

( * ) Notice: Subject to any disclaimer, the term of this patent is extended or adjusted under 35 U.S.C. 154(b) by 386 days.

(21) Appl. No.: 16/330,537

(22) PCT Filed: Sep. 5, 2017

(86) PCT No.: PCT/JP2017/031880
§ 371 (c)(1),
(2) Date: Mar. 5, 2019

(87) PCT Pub. No.: WO2018/047798
PCT Pub. Date: Mar. 15, 2018

(65) Prior Publication Data
US 2021/0228461 A1  Jul. 29, 2021

(30) Foreign Application Priority Data
Sep. 6, 2016  (JP) .............................. JP2016-173276

(51) Int. Cl.
*A61K 8/44* (2006.01)
*A61K 8/34* (2006.01)
*A61K 8/41* (2006.01)
*A61K 8/43* (2006.01)
*A61K 8/46* (2006.01)
*A61Q 11/00* (2006.01)

(52) U.S. Cl.
CPC .............. *A61K 8/442* (2013.01); *A61K 8/345* (2013.01); *A61K 8/416* (2013.01); *A61K 8/43* (2013.01); *A61K 8/463* (2013.01); *A61Q 11/00* (2013.01); *A61K 2800/30* (2013.01); *A61K 2800/5922* (2013.01)

(58) Field of Classification Search
CPC ... A61K 8/34; A61K 8/30; A61K 8/24; A61Q 11/00
USPC .......................................................... 424/49
See application file for complete search history.

(56) References Cited

U.S. PATENT DOCUMENTS

| | | | | |
|---|---|---|---|---|
| 2,909,535 A | * | 10/1959 | Jungermann | .......... A61Q 11/00 554/63 |
| 2009/0269287 A1 | * | 10/2009 | Berta | ....................... A61K 8/73 424/52 |
| 2015/0098911 A1 | * | 4/2015 | Saito | ....................... A61K 8/60 424/56 |

FOREIGN PATENT DOCUMENTS

| | | |
|---|---|---|
| JP | 60-92208 A | 5/1985 |
| JP | 10-291921 A | 11/1998 |
| JP | 2013-112654 A | 6/2013 |
| JP | 2013-203676 A | 10/2013 |
| JP | 2013-253064 A | 12/2013 |
| JP | 2014-12655 A | 1/2014 |
| JP | 2014-125443 A | 7/2014 |
| JP | 2016-37455 A | 3/2016 |
| WO | WO 2015/151916 A1 | 10/2015 |

OTHER PUBLICATIONS

International Search Report dated Oct. 24, 2017 in PCT/JP2017/031880 filed on Sep. 5, 2017.

* cited by examiner

Primary Examiner — Walter E Webb
(74) Attorney, Agent, or Firm — Oblon, McClleland, Maier & Neustadt, L.L.P.

(57) ABSTRACT

The present invention relates to an oral composition having excellent stability and persistence of moderate foaming while sufficiently dispersing biofilm firmly adhered to a tooth surface and showing a good bactericidal effect. That is, the present invention provides an oral composition comprising the following ingredients (A), (B), (C), and (D): (A) 0.001 mass % or more and 0.3 mass % or less of myristoyl glutamic acid or a salt thereof; (B) 0.001 mass % or more and 0.3 mass % or less of lauroyl glutamic acid or a salt thereof; (C) an alkylsulfate; and (D) water, wherein a mass ratio of the content of ingredient (A) to the content of ingredient (B), ((A)/(B)), is 0.25 or more and 4 or less; and the content of a polyphosphoric acid or a salt thereof is 0.01 mass % or less.

17 Claims, No Drawings

ORAL COMPOSITION

FIELD OF THE INVENTION

The present invention relates to an oral composition.

BACKGROUND OF THE INVENTION

It is conventionally known that use of anionic surfactants in oral compositions is effective for enhancing dispersibility or solubility of each ingredient and ensuring foaming performance and improving cleansing effect. In particular, alkylsulfates have been widely used as those having good foamability.

N-acylamino acids or salts thereof are also anionic surfactants and are also known that they can further provide effects of removing dirt, stains, and so on from teeth and preventing them from adhering to teeth. For example, Patent Literatures 1 and 2 disclose compositions containing, together with an N-acylamino acid or a salt thereof, pyrophosphoric acid or a salt thereof or an alkylsulfate and a polyphosphoric acid or a salt thereof for enhancing effects of removing protein stains and preventing protein stains from adhering. Patent Literature 3 discloses a composition containing an alkylsulfate, a specific water-soluble polyphosphate, and polyethylene glycol together with an N-acylamino acid or a salt thereof for improving effects of suppressing adhesion of stains and removing stains.

(Patent Literature 1) JA-A-2014-12655
(Patent Literature 2) JA-A-2013-253064
(Patent Literature 3) JA-A-2013-112654

The present invention provides an oral composition comprising the following ingredients (A), (B), (C), and (D):
(A) 0.001 mass % or more and 0.3 mass % or less of myristoyl glutamic acid or a salt thereof;
(B) 0.001 mass % or more and 0.3 mass % or less of lauroyl glutamic acid or a salt thereof;
(C) an alkylsulfate; and
(D) water,
wherein a mass ratio of the content of ingredient (A) to the content of ingredient (B), ((A)/(B)), is 0.25 or more and 4 or less; and
the content of a polyphosphoric acid or a salt thereof is 0.01 mass % or less.

In effective removal of biofilm formed by various bacteria present in the oral cavity, the ingredients contained in each composition in the technologies described in the above-mentioned Patent Literatures are merely adsorbed to the surface layer of the biofilm or the vicinity thereof, and further improvement is still necessary to fragment and effectively disperse biofilm. In addition, although excellent foamability such as good foaming can be shown, it has not been investigated yet for imparting performance of persisting moderate foaming without excessive foaming.

Accordingly, the present invention relates to an oral composition having excellent stability and persistence of moderate foaming while sufficiently dispersing biofilm firmly adhered to a tooth surface and showing a good bactericidal effect.

The present inventor accordingly conducted various studies and found that an oral composition capable of providing not only excellent biofilm dispersibility but also a good bactericidal effect and also stably and persistently providing moderate foaming in various forms of use by containing a combination of two N-acylamino acids or salts thereof consisting of specific amounts of myristoyl glutamic acid or a salt thereof and lauroyl glutamic acid or a salt thereof at a specific mass ratio and simultaneously a restricted content of a polyphosphoric acid or a salt thereof.

The oral composition of the present invention can effectively permeate in biofilm firmly adhered to a tooth surface from the surface layer to the deep part thereof to disperse the biofilm and can enhance and accelerate the bactericidal effect. In addition, moderate foaming can be stably provided without excessive foaming, and it is therefore possible to express a good feeling upon use and cleaning effect even in a form of time-consuming use.

DETAILED DESCRIPTION OF THE INVENTION

The present invention will now be described below in detail.

The oral composition of the present invention comprises 0.001 mass % or more and 0.3 mass % or less of myristoyl glutamic acid or a salt thereof as ingredient (A). The ingredient (A) is one kinds of so-called N-acylamino acid or a salt thereof. When ingredient (A) is singly used, it merely acts on the surface layer of biofilm or the vicinity thereof. However, when it is used together with ingredient (B), which is also an N-acylamino acid or a salt thereof and will be described below, at specific amounts respectively, they effectively act on not only the surface layer but also the deep part of biofilm firmly adhered to a tooth surface and not only can fragment and disperse the biofilm, which is an aggregate of proliferated bacteria, but also can synergistically enhance the bactericidal effects possessed by them. Use of these ingredient (A) and ingredient (B), in combination with an alkylsulfate as ingredient (C) described later, can stably provide moderate foaming, while preventing an excessive increase of foam. For example, it is therefore possible to persist good foaming and obtain a comfortable feeling upon use and actual cleaning feeling even in a form of time-consuming use, such as repetition of leaving the composition after brushing or gargling at a predetermined part in the oral cavity.

The content of ingredient (A) in the oral composition of the present invention is 0.001 mass % or more, preferably 0.005 mass % or more, more preferably 0.01 mass % or more from the viewpoint of showing excellent biofilm-dispersing and bactericidal effects in combination with ingredient (B). In addition, the content of ingredient (A) in the oral composition of the preset invention is 0.3 mass % or less, preferably 0.27 mass % or less, more preferably 0.24 mass % or less from the viewpoint of ensuring stability and persistence of moderate foaming in combination with ingredient (B). The content of ingredient (A) in the oral composition of the present invention is 0.001 mass % or more and 0.3 mass % or less, preferably from 0.005 to 0.27 mass %, more preferably from 0.01 to 0.24 mass %.

The oral composition of the present invention comprises 0.001 mass % or more and 0.3 mass % or less of lauroyl glutamic acid or a salt thereof as ingredient (B). Consequently, the composition shows an excellent biofilm-dispersing effect in combination with ingredient (A) described above and can effectively enhance the bactericidal effect and stably and persistently provide moderate foaming.

The content of ingredient (B) in the oral composition of the present invention is 0.001 mass % or more, preferably 0.005 mass % or more, more preferably 0.01 mass % or more from the viewpoint of showing excellent biofilm-dispersing and bactericidal effects in combination with ingredient (A). In addition, the content of ingredient (B) in the oral composition of the present invention is 0.3 mass % or less, preferably 0.27 mass % or less, more preferably 0.24 mass % or less from the viewpoint of ensuring stability and persistence of moderate foaming in combination with ingredient (A). The content of ingredient (B) in the oral composition of the present invention is 0.001 mass % or more and 0.3 mass % or less, preferably from 0.005 to 0.27 mass %, more preferably from 0.01 to 0.24 mass %.

A mass ratio of the content of ingredient (A) to the content of ingredient (B), ((A)/(B)), is 0.25 or more, preferably 0.4 or more, more preferably 0.6 or more, further preferably 0.75 or more, further preferably 0.9 or more from the viewpoint of showing an excellent bactericidal effect. In addition, a mass ratio of the content of ingredient (A) to the content of ingredient (B), ((A)/(B)), is 4 or less, preferably 3.2 or less, more preferably 2.5 or less, further preferably 1.4 or less, further preferably 1.1 or less from the viewpoint of ensuring stability and persistence of moderate foaming. A mass ratio of the content of ingredient (A) to the content of ingredient (B), ((A)/(B)), is 0.25 or more and 4 or less, preferably from 0.4 to 3.2, more preferably from 0.6 to 2.5, further preferably from 0.75 to 1.4, further preferably from 0.9 to 1.1.

The total content of ingredients (A) and (B) in the oral composition of the present invention is preferably 0.005 mass % or more, more preferably 0.01 mass % or more, further preferably 0.015 mass % or more from the viewpoint of ensuring excellent biofilm-dispersing and bactericidal effects. In addition, the total content of ingredients (A) and (B) in the oral composition of the present invention is preferably 0.5 mass % or less, more preferably 0.35 mass % or less, further preferably 0.2 mass % or less from the viewpoint of preventing an excessive decrease in foaming and the viewpoint of ensuring low irritation and persisting a good feeling upon use. The total content of ingredients (A) and (B) in the oral composition of the present invention is preferably from 0.005 to 0.5 mass %, more preferably from 0.01 to 0.35 mass %, further preferably from 0.03 to 0.2 mass %.

The oral composition of the present invention comprises an alkylsulfate as ingredient (C). Consequently, it is possible to suppress excessive foaming and to effectively show stability and persistence of moderate foaming in combination with ingredients (A) and (B), while ensuring good foamability and preventing unnecessary defoaming when using. The ingredient (C) is preferably one or more selected from the group consisting of sodium lauryl sulfate, sodium myristyl sulfate, sodium palmityl sulfate, sodium stearyl sulfate, sodium octyl sulfate, and sodium capryl sulfate. Among them, sodium lauryl sulfate is preferred from the viewpoint of showing excellent foaming and the viewpoint of imparting good cleaning performance and availability.

The content of ingredient (C) in the oral composition of the present invention is preferably 0.01 mass % or more, more preferably 0.03 mass % or more, further preferably 0.05 mass % or more from the viewpoint of ensuring good foamability. In addition, the content of ingredient (C) in the oral composition of the present invention is preferably 3 mass % or less, more preferably 2.5 mass % or less, further preferably 2 mass % or less from the viewpoint of effectively suppressing excessive foaming. The content of ingredient (C) in the oral composition of the present invention is preferably from 0.01 to 3 mass %, more preferably from 0.03 to 2.5 mass %, further preferably from 0.05 to 2 mass %.

A mass ratio of the total content of ingredients (A) and (B) to the content of ingredient (C), (({(A)+(B)}/(C)), is preferably 0.005 or more, more preferably 0.01 or more, further preferably 0.02 or more, further preferably 0.03 or more from the viewpoint of satisfactorily having both excellent biofilm-dispersing and bactericidal effects. In addition, the mass ratio of the total content of ingredients (A) and (B) to the content of ingredient (C), ({(A)+(B)}/(C)), is preferably 4 or less, more preferably 1 or less, further preferably 0.5 or less, further preferably 0.08 or less from the viewpoint of ensuring expression of stability and persistence of moderate foaming. The mass ratio of the total content of ingredients (A) and (B) to the content of ingredient (C), ({(A)+(B)}/(C)), is preferably from 0.005 to 4, more preferably from 0.01 to 1, further preferably from 0.02 to 0.5, further preferably from 0.03 to 0.08.

The oral composition of the present invention comprises water as ingredient (D). The term "water" as ingredient (D) in the present invention refers to the total water contained in the oral composition including not only, for example, purified water blended in the oral composition but also water contained in each of the blended ingredients such as a 70% sorbitol liquid (aqueous solution) and a 48% potassium hydroxide liquid (aqueous solution) used in formulating. The oral composition thus-containing water as ingredient (D) can satisfactorily disperse or dissolve each ingredient and express stability and persistence of moderate foaming, while ensuring excellent biofilm-dispersing and bactericidal effects.

For example, when the oral composition of the present invention is a dentifrice composition such as toothpaste or powder dentifrice, the content of ingredient (D) in the oral composition of the present invention is preferably 5 mass % or more, more preferably 8 mass % or more, further preferably 12 mass % or more, further preferably 15 mass % or more and preferably 50 mass % or less, more preferably 40 mass % or less, further preferably 30 mass % or less.

When the oral composition of the present invention is a dentifrice composition, a mass ratio of the content of ingredient (A) to the content of ingredient (D), ((A)/(D)), is preferably 0.0005 or more, more preferably 0.0007 or more, further preferably 0.0009 or more from the viewpoint of satisfactorily dissolving or dispersing ingredient (A) in the composition and sufficiently showing excellent biofilm-dispersing and bactericidal effects of ingredient (A). In addition, when the oral composition of the present invention is a dentifrice composition, the mass ratio of the content of ingredient (A) to the content of ingredient (D), ((A)/(D)), is preferably 0.01 or less, more preferably 0.008 or less, further preferably 0.005 or less from the viewpoint of ensuring stability and persistence of moderate foaming while showing the biofilm-dispersing and bactericidal effects of ingredient (A).

Furthermore, when the oral composition of the present invention is a dentifrice composition, a mass ratio of the content of ingredient (B) to the content of ingredient (D), ((B)/(D)), is preferably 0.0005 or more, more preferably 0.0007 or more, further preferably 0.0009 or more from the viewpoint of satisfactorily dissolving or dispersing ingredient (B) in the composition and sufficiently showing the biofilm-dispersing and bactericidal effects of ingredient (B). In addition, when the oral composition of the present invention is a dentifrice composition, the mass ratio of the content of ingredient (B) to the content of ingredient (D), ((B)/(D)), is preferably 0.01 or less, more preferably 0.008 or less, further preferably 0.005 or less from the viewpoint of ensuring stability and persistence of moderate foaming while showing the biofilm-dispersing and bactericidal effects of ingredient (B).

When the oral composition of the present invention is a liquid oral composition such as mouthwash or liquid dentifrice, the content of ingredient (D) in the oral composition of the present invention is preferably 90 mass % or less, more preferably 80 mass % or less and preferably 70 mass % or more.

In addition, when the oral composition of the present invention is a liquid oral composition, the mass ratio of the content of ingredient (A) to the content of ingredient (D), ((A)/(D)), is preferably 0.0001 or more, more preferably 0.0002 or more, further preferably 0.0003 or more from the viewpoint of satisfactorily dissolving or dispersing ingredient (A) in the composition and sufficiently showing the desired effects of ingredient (A). In addition, when the oral composition of the present invention is a liquid oral composition, the mass ratio of the content of ingredient (A) to the content of ingredient (D), ((A)/(D)), is preferably 0.01 or less, more preferably 0.007 or less, further preferably 0.004 or less from the viewpoint of ensuring stability and persistence of moderate foaming while showing the desired effects of ingredient (A).

Furthermore, when the oral composition of the present invention is a liquid oral composition, the mass ratio of the content of ingredient (B) to the content of ingredient (D), ((B)/(D)), is preferably 0.0001 or more, more preferably 0.0002 or more, further preferably 0.0003 or more from the viewpoint of satisfactorily dissolving or dispersing ingredient (A) in the composition and sufficiently showing the desired effects of ingredient (B). In addition, when the oral composition of the present invention is a liquid oral composition, the mass ratio of the content of ingredient (B) to the content of ingredient (D), ((B)/(D)), is preferably 0.01 or less, more preferably 0.007 or less, further preferably 0.004 or less from the viewpoint of ensuring stability and persistence of moderate foaming while showing the desired effects of ingredient (A).

The content of ingredient (D), i.e., the water content in the oral composition of the present invention can be calculated from the content of the blended water and the content of water in the blended ingredients, and the content can also be measured with, for example, a Karl Fischer moisture titrator. As the Karl Fischer moisture titrator, for example, a trace moisture measuring device (Hiranuma Sangyo Co., Ltd.) can be used. By using this device, 5 g of a dentifrice composition is suspended in 25 g of anhydrous methanol, and the water content in 0.02 g of this suspension can be measured.

In the oral composition of the present invention, the content of a polyphosphoric acid or a salt thereof is 0.01 mass % or less. Such limitation in the content of the polyphosphoric acid or a salt thereof can effectively prevent a decrease in the biofilm-dispersing effect and the bactericidal effect provided by the combination of ingredient (A) and ingredient (B). Examples of the polyphosphoric acid include pyrophosphoric acid, tripolyphosphoric acid, tetrapolyphosphoric acid, and metaphosphoric acid; and examples of the salt of the polyphosphate is a sodium salt and a potassium salt.

The content of the polyphosphoric acid or a salt thereof in the oral composition of the present invention is 0.01 mass % or less, preferably 0.005 mass % or less, more preferably 0.001 mass % or less from the viewpoint of effectively preventing the bactericidal effect on biofilm from being decreased and fragmenting the biofilm and effectively dispersing it. Alternatively, the oral composition of the present invention preferably does not contain the polyphosphoric acid or a salt thereof.

The oral composition of the present invention preferably further contains (E) a cationic bactericide. In the composition containing ingredient (E), ingredient (E), together with ingredient (A) and ingredient (B), can easily act on the details of biofilm satisfactorily dispersed by ingredient (A) and ingredient (B), and can further enhance the bactericidal effect on the entire region of the biofilm.

The cationic bactericide is, for example, one or more selected from quaternary ammonium compounds and biguanide compounds. The bactericide belonging to the quaternary ammonium compound is specifically, for example, one or more selected from the group consisting of cetylpyridinium chloride, benzethonium chloride, dequalinium chloride, benzalkonium chloride, alkyldimethylammonium chloride, alkyltrimethylammonium chloride, and methylbenzethonium chloride. The bactericide belonging to the biguanide compound is specifically, for example, one or more selected from chlorhexidine and salts thereof. Among them, the cationic bactericide is preferably a quaternary ammonium compound, preferably one or more selected from cetylpyridinium chloride and benzethonium chloride, and further preferably cetylpyridinium chloride from the viewpoint of enhancing the bactericidal effect in combination with ingredient (A) and ingredient (B) and the viewpoint of effectively showing a high bactericidal effect on the entire region of biofilm.

The content of ingredient (E) in the oral composition of the present invention is preferably 0.005 mass % or more, more preferably 0.007 mass % or more from the viewpoint of effectively showing the bactericidal effect. In addition, the content of ingredient (E) in the oral composition of the present invention is preferably 0.1 mass % or less, more preferably 0.08 mass % or less from the viewpoint of ensuring a good feeling upon use. The content of ingredient (E) in the oral composition of the present invention is preferably from 0.005 to 0.1 mass %, more preferably from 0.007 to 0.08 mass %.

A mass ratio of the content of ingredient (A) to the content of ingredient (E), ((A)/(E)), is preferably 0.1 or more, more preferably 0.3 or more, further preferably 0.8 or more from the viewpoint of showing an excellent bactericidal effect. In addition, the mass ratio of the content of ingredient (A) to the content of ingredient (E), ((A)/(E)), is preferably 30 or less, more preferably 20 or less, further preferably 12 or less from the viewpoint of enhancing stability and persistence of moderate foaming. The mass ratio of the content of ingredient (A) to the content of ingredient (E), ((A)/(E)), is preferably from 0.1 to 30, more preferably from 0.3 to 20, further preferably from 0.8 to 12.

A mass ratio of the total content of ingredients (A) and (B) to the content of ingredient (E), ({(A)+(B)}/(E)), is preferably 0.5 or more, more preferably 0.8 or more, further preferably 2 or more from the viewpoint of satisfactorily having both excellent biofilm-dispersing and bactericidal effects. In addition, the mass ratio of the total content of ingredients (A) and (B) to the content of ingredient (E), ({(A) B)}/(E)), is 80 or less, more preferably 50 or less, further preferably 25 or less from the viewpoint of ensuring expression of stability and persistence of moderate foaming. The mass ratio of the total content of ingredients (A) and (B) to the content of ingredient (E), ({(A)+(B)}/(E)), is preferably from 0.5 to 80, more preferably from 0.8 to 50, further preferably from 2 to 25.

The oral composition of the present invention preferably further contains (F) erythritol. In the composition containing ingredient (F), it is possible to further enhance the biofilm-dispersing effect and the bactericidal effect shown by the combination of ingredient (A) and ingredient (B). When the oral composition of the present invention is a dentifrice composition, the content of ingredient (F) in the oral composition of the present invention is preferably 5 mass % or more, more preferably 10 mass % or more, further preferably 20 mass % or more from the viewpoint of effectively enhancing the biofilm-dispersing effect and the bactericidal effect. In addition, the content of ingredient (F) in the oral composition of the present invention is preferably 60 mass % or less, more preferably 55 mass % or less, further preferably 50 mass % or less from the viewpoint of ensuring stability and persistence of moderate foaming. The content of ingredient (F) in the oral composition of the present invention is preferably from 5 to 60 mass %, more preferably from 10 to 55 mass %, further preferably from 20 to 50 mass %.

When the oral composition of the present invention is a liquid oral composition, the content of ingredient (F) in the oral composition of the present invention is preferably 1 mass % or more from the viewpoint of effectively enhancing the biofilm-dispersing effect and the bactericidal effect. In addition, the content of ingredient (F) in the oral composition of the present invention is preferably 60 mass % or less, more preferably 30 mass % or less, further preferably 15 mass % or less from the viewpoint of ensuring stability and persistence of moderate foaming. The content of ingredient (F) in the oral composition of the present invention is preferably from 1 to 60 mass %, more preferably from 1 to 30 mass %, further preferably from 1 to 15 mass %.

When the oral composition of the present invention is a dentifrice composition, the composition preferably further contain a binder. The binder may be one or more selected from the group consisting of sodium alginate, sodium carboxymethyl cellulose, carrageenan, xanthan gum, sodium polyacrylate, hydroxyethyl cellulose, hydroxypropyl cellulose, pectin, gum tragacanth, gum arabic, guar gum, karaya gum, locust bean gum, gellan gum, tamarid gum, psyllium seed gum, polyvinyl alcohol, sodium chondroitin sulfate, and methoxyethylene maleic anhydride copolymers. Among them, the binder is preferably one or more, more preferably two or more, selected from sodium carboxymethyl cellulose having a degree of etherification of 0.7 to 2.0, carrageenan, and xanthan gum. The content of the binder in the oral composition of the present invention is preferably 0.05 mass % or more, more preferably 0.1 mass % or more and preferably 2 mass % or less, more preferably 1.5 mass % or less. In addition, when the oral composition of the present invention is a dentifrice composition, it is preferable to contain, together with the binder, 1 mass % or more and 20 mass % or less of thickening silica (having an oil absorption of 200 to 400 mL/100 g measured by a method in accordance with JIS K5101-13-2).

When the oral composition of the present invention is a dentifrice composition, the viscosity at 20° C. is preferably from 500 to 10000 dPa·s, further preferably from 1000 to 4000 dPa·s. By controlling the viscosity to 10000 dPa·s or less, the structural viscosity of the composition can be imparted by an undissolved sugar alcohol. The viscosity of a dentifrice composition can be obtained by filling the composition in a chamber for viscosity measurement, then preserving it in an incubator of 20° C. for 24 hours, and measuring its viscosity using a Helipath viscometer (B-type viscometer) and a rotor H7 at a rotation speed of 2.5 rpm for 1 minute.

When the oral composition of the present invention is a dentifrice composition, a reduction rate of the viscosity (20° C.) when adding 25 parts by mass of water to 100 parts by mass of the dentifrice composition is preferably 10% or less, more preferably from 1% to 10%, further preferably from 3% to 8%, further preferably from 3% to 7% with respect to the viscosity (20° C.) of the undiluted one before water is added. Since the dentifrice composition of the present invention is provided by an undissolved sugar alcohol with structural viscosity, the reduction rate of the viscosity by addition of water is large. In a preferred embodiment, a saliva dilution model during tooth brushing in which 100 parts by mass of a composition is diluted with 25 parts by mass of water shows that the viscosity of the diluted composition decreases to 10% or less, and the fluoride ions in water (D) can be therefore applied to teeth with a high concentration and fluidity. From this viewpoint, the viscosity measured within 1 hour after adding water is used as the viscosity (20° C.) when adding 25 parts by mass of water.

When the oral composition of the present invention is a dentifrice composition, the composition preferably further contain an abrasive within a range that does not impair the effects of the present invention. Examples of the abrasive include calcium phosphate, calcium hydrogen phosphate, calcium carbonate, aluminum hydroxide, aluminum silicate, zirconium silicate, abrasive silica (having an oil absorption of 50 to 150 mL/100 g measured by a method in accordance with JIS K5101-13-2) and the like. An abrasive having an RDA value (Radioactive Dentine Abrasion value, a value measure by Protocol A, Test Method for Abrasiveness, ISO 11609) of 20 to 250 is generally used.

The oral composition of the present invention can further contain a sugar alcohol other than xylitol and ingredient (F), such as sorbitol, erythritol, reduced palatinose, or mannitol; a fluoride such as sodium fluoride, potassium fluoride, ammonium fluoride, or hydrofluoric acid hexylamine, or a fluorine-containing compound such as monofluorophosphoric acid; an ingredient for dentin hypersensitivity such as hydroxyapatite; a wetting agent, such as glycerol, polyethylene glycol, or propylene glycol; a flavoring agent; a medicinal ingredient such as a bactericide other than ingredient (E) or an anti-inflammatory agent; a preservative; a plant extract; and another active ingredient, within a range that does not impair the effects of the present invention.

The oral composition of the present invention may be a dentifrice composition such as toothpaste or powder dentifrice, or a liquid oral composition such as mouthwash or liquid dentifrice, and is preferably a dentifrice composition from the viewpoint of capable of realizing moderate foaming with excellent feeling upon use and actual cleaning feeling and high stability and persistence, in addition to both the excellent biofilm-dispersing effect and bactericidal effects possessed by the oral composition of the present invention.

With respect to the above-described embodiments of the present invention, the following oral compositions are further disclosed.

[1] An oral composition comprising the following ingredients (A), (B), (C), and (D):
(A) 0.001 mass % or more and 0.3 mass % or less of myristoyl glutamic acid or a salt thereof;
(B) 0.001 mass % or more and 0.3 mass % or less of lauroyl glutamic acid or a salt thereof;
(C) an alkylsulfate; and
(D) water
wherein a mass ratio of the content of ingredient (A) to the content of ingredient (B), ((A)/(B)), is 0.25 or more and 4 or less; and
the content of a polyphosphoric acid or a salt thereof is 0.01 mass % or less.

[2] The oral composition according to aspect [1], wherein the content of ingredient (A) is preferably 0.005 mass % or more, more preferably 0.01 mass % or more and preferably 0.27 mass % or less, more preferably 0.24 mass % or less.

[3] The oral composition according to aspect [1] or [2], wherein the content of ingredient (B) is preferably 0.005 mass % or more, more preferably 0.01 mass % or more and preferably 0.27 mass % or less, more preferably 0.24 mass % or less.

[4] The oral composition according to any one of aspects [1] to [3], wherein the mass ratio of the content of ingredient (A) to the content of ingredient (B), ((A)/(B)), is preferably 0.4 or more, more preferably 0.6 or more, further preferably 0.75 or more, further preferably 0.9 or more and preferably 3.2 or less, more preferably 2.5 or less, further preferably 1.4 or less, further preferably 1.1 or less.

[5] The oral composition according to any one of aspects [1] to [4], wherein the total content of ingredients (A) and (B) is preferably 0.005 mass % or more, more preferably 0.01 mass % or more, further preferably 0.015 mass % or more and preferably 0.5 mass % or less, more preferably 0.35 mass % or less, further preferably 0.2 mass % or less.

[6] The oral composition according to any one of aspects [1] to [5], wherein the content of ingredient (C) is preferably 0.01 mass % or more, more preferably 0.03 mass % or more, further preferably 0.05 mass % or more and preferably 3 mass % or less, more preferably 2.5 mass % or less, further preferably 2 mass % or less.

[7] The oral composition according to any one of aspects [1] to [6], wherein the content of a polyphosphoric acid or a salt thereof is preferably 0.005 mass % or less, more preferably 0.001 mass % or less; or the oral composition preferably does not contain a polyphosphoric acid or a salt thereof.

[8] The oral composition according to any one of aspects [1] to [7], wherein a mass ratio of the total content of ingredients (A) and (B) to the content of ingredient (C), ({(A)+(B)}/(C)), is preferably 0.005 or more, more preferably 0.01 or more, further preferably 0.02 or more, further preferably 0.03 or more and preferably 4 or less, more preferably 1 or less, further preferably 0.5 or less, further preferably 0.08 or less.

[9] The oral composition according to any one of aspects [1] to [8], wherein when the oral composition of the present invention is a dentifrice composition, the content of ingredient (D) is preferably 5 mass % or more, more preferably 8 mass % or more, further preferably 12 mass % or more, further preferably 15 mass % or more and preferably 50 mass % or less, more preferably 40 mass % or less, further preferably 30 mass % or less.

[10] The oral composition according to aspect [9], wherein a mass ratio of the content of ingredient (A) to the content of ingredient (D), ((A)/(D)), is preferably 0.0005 or more, more preferably 0.0007 or more, further preferably 0.0009 or more and preferably 0.01 or less, more preferably 0.008 or less, further preferably 0.005 or less.

[11] The oral composition according to aspect [9] or [10], wherein a mass ratio of the content of ingredient (B) to the content of ingredient (D), ((B)/(D)), is preferably 0.0005 or more, more preferably 0.0007 or more, further preferably 0.0009 or more and preferably 0.01 or less, more preferably 0.008 or less, further preferably 0.005 or less.

[12] The oral composition according to any one of aspects [1] to [8], wherein when the oral composition of the present invention is a liquid oral composition, the content of ingredient (D) is preferably 90 mass % or less, more preferably 80 mass % or less and preferably 70 mass % or more.

[13] The oral composition according to aspect [12], wherein a mass ratio of the content of ingredient (A) to the content of ingredient (D), ((A)/(D)), is preferably 0.0001 or more, preferably 0.0002 or more, further preferably 0.0003 or more and preferably 0.01 or less, more preferably 0.007 or less, further preferably 0.004 or less.

[14] The oral composition. according to aspect [12] or [13], wherein a mass ratio of the content of ingredient (B) to the content of ingredient (D), ((B)/(D)), is preferably 0.0001 or more, more preferably 0.0002 or more, further preferably 0.0003 or more and preferably 0.01 or less, more preferably 0.007 or less, further preferably 0.004 or less.

[15] The oral composition according to any one of aspects [1] to [14], wherein the composition preferably further comprises (E) a cationic bactericide, wherein ingredient (E) is preferably one or more selected from the group consisting of a quaternary ammonium compound and biguanide compound.

[16] The oral composition according to aspect [15], wherein a mass ratio of the content of ingredient (A) to the content of ingredient (E), ((A)/(E)), is preferably 0.1 or more, more preferably 0.3 or more, further preferably 0.8 or more and preferably 30 or less, more preferably 20 or less, further preferably 12 or less.

[17] The oral composition according to aspect [15] or [16], wherein a mass ratio of the total content of ingredients (A) and (B) to the content of ingredient (E), ({(A)+(B)}/(E)), is preferably 0.5 or more, more preferably 0.8 or more, further preferably 2 or more and preferably 80 or less, more preferably 50 or less, further preferably 25 or less.

[18] The oral composition according to any one of aspects [1] to [17], wherein the composition preferably further comprises (F) erythritol, wherein when the oral composition of the present invention is a dentifrice composition, the content of ingredient (F) is preferably 5 mass % or more, more preferably 10 mass % or more, further preferably 20 mass % or more and preferably 60 mass % or less, more preferably 55 mass % or less, further preferably 50 mass % or less; while when the oral composition of the present invention is a liquid oral composition, the content of ingredient (F) is preferably 1 mass % or more and preferably 60 mass % or less, more preferably 30 mass % or less, further preferably 15 mass % or less.

[19] The oral composition according to any one of aspects [1] to [18], wherein when the oral composition of the present invention is a dentifrice composition, the viscosity at 20° C. is preferably from 500 to 10000 dPa·s, further preferably from 1000 to 4000 dP·s.

[20] The oral composition according to any one of aspects [1] to [19], wherein the composition is toothpaste or powder dentifrice.

[21] The oral composition according to any one of aspects [1] to [19], wherein the composition is mouthwash or liquid dentifrice.

EXAMPLES

The present invention will now be specifically described based on Examples. The content of each ingredient is represented by mass % unless otherwise specified in the Tables.

Examples 1 to 9 and Comparative Examples 1 to 6

Each liquid oral composition was prepared according to the formulations shown in Tables 1 and 2. The biofilm-dispersing effect, bactericidal effect, and stability and persistence of foaming were evaluated using the resulting liquid oral compositions according to the following methods.

The results are shown in Tables 1 and 2.

<<Biofilm-Dispersing Effect>>

1) Production of Biofilm Model

Stimulating saliva was collected in a Falcon tube and was centrifugated at 3000 rpm and room temperature for 10 minutes. Sucrose was added to the separated supernatant saliva so as to give a 5 mass % solution, followed by stirring with a stirrer (Vortex, manufactured by Nippon Genetics Co., Ltd.) to prepare a biofilm model test solution.

Subsequently, one surface of each HAp substrate (manufactured by Cosmo Bio, 1 cm square) was mirror-polished with abrasive paper of 40 μm, 12 μm, and 3 μm, and the substrates were then immersed in 1N HCl for 1 minute for acid decalcification treatment. The-thus treated HAp substrates were put in a 24-well plate, and 1 mL of the biofilm model test solution prepared above was added to each well. The plate was then stored in a plastic case together with a $CO_2$ pack to achieve anaerobic condition, and culturing was performed at 37° C. for 15 hours.

2) Evaluation of Biofilm-Dispersing Effect

After formation of the resulting biofilm model on each 1-cm square Hap substrate, 0.5 mL of each liquid oral composition diluted 4-fold with purified water (assumption of dilution with saliva and so on in actual use of the oral composition) was then added to each well. After shaking for 3 minutes, the plate was washed with phosphate buffered saline once. Subsequently, after dyeing with a Red-coat dyeing solution, the plate was washed with phosphate buffered saline once, and the absorbance (540 nm) of a test solution extracted with NaOH (1N) was measured.

The dispersion ratio (%) with respect to untreated biofilm was calculated from the measured value and was used as an index for the evaluation of biofilm-dispersing effect. A higher value means a higher biofilm-dispersing effect.

<<Bactericidal Effect>>

1) Production of Biofilm Model

A biofilm model was produced as in the biofilm model produced in the "Biofilm-dispersing effect" except that the culture time was changed to 13 hours.

2) Evaluation of Bactericidal Effect

After formation of the resulting biofilm model on a 24-well plate and washing with ion exchanged water, 0.5 mL of each liquid oral composition diluted 4-fold with purified water (assumption of dilution with saliva and so on in actual use of the oral composition) was then added to each well, followed by leaving to stand for 3 minutes. Subsequently, after the plate was washed with phosphate buffered saline twice and dyed with a Live/dead dyeing solution, the ratio of fluorescence intensities of living bacteria and killed bacteria was measured.

The viability (%) with respect to phosphate buffered saline treatment was calculated from the measured value and was used as an index for the evaluation of bactericidal effect. A lower value means a higher bactericidal effect.

<<Foaming Stability and Persistence>>

After 1 mL of each liquid oral composition diluted 4-fold with purified water prepared for the above-described evaluation was put in a test tube and was shaken with the hand for 10 seconds, it was leaved to stand for 10 minutes, and then the height of foam was read. This series of operations was repeated three times. Subsequently, the rate of change in the height of foam, (Δfoam), in each test solution was calculated using the following formula and was used as an index for the evaluation of foaming stability and persistence.

When the value was within a range of from −0.05 to 0.05, it was judged that moderate foaming was provided without excessive foaming and was excellent in stability and persistence.

Rate of change in height of foam (Δfoam)={(height of third foam)−(height of first foam)}/(height of first foam)

TABLE 1

|  |  | Example 1 | Example 2 | Example 3 | Example 4 | Example 5 | Example 6 | Comparative Example 1 | Comparative Example 2 | Comparative Example 3 |
|---|---|---|---|---|---|---|---|---|---|---|
| (A) | Sodium myristoyl glutamate*[1] | 0.025 | 0.1 | 0.2 | 0.075 | 0.04 | 0.06 | 0.1 | 0 | 0.025 |
| (B) | Sodium lauroyl glutamate*[2] | 0.025 | 0.1 | 0.2 | 0.025 | 0.06 | 0.04 | 0 | 0.1 | 0.025 |
| (C) | Sodium lauryl sulfate | 1.3 | 1.3 | 1.3 | 1.3 | 1.3 | 1.3 | 1.3 | 1.3 | 1.3 |
|  | Sodium fluoride | 0 | 0 | 0 | 0 | 0 | 0 | 0 | 0 | 0 |
| (E) | Cetylpyridinium chloride | 0.02 | 0.02 | 0.02 | 0.02 | 0.02 | 0.02 | 0.02 | 0.02 | 0.02 |
|  | Dipotassium glycyrrhizinate | 0 | 0 | 0 | 0 | 0 | 0 | 0 | 0 | 0 |
| (F) | Erythritol | 40 | 40 | 40 | 40 | 40 | 40 | 40 | 40 | 40 |
|  | Sodium pyrophosphate, anhydrous | 0 | 0 | 0 | 0 | 0 | 0 | 0.02 | 0 | 0.02 |
| (D) | Purified water | 59.98 | 59.98 | 59.98 | 59.98 | 59.98 | 59.98 | 59.96 | 59.98 | 59.96 |
|  | Total | 100 | 100 | 100 | 100 | 100 | 100 | 100 | 100 | 100 |
|  | (A)/(B) | 1.00 | 1.00 | 1.00 | 3.00 | 0.67 | 1.50 | — | 0.00 | 1.00 |
|  | (A) + (B) | 0.05 | 0.20 | 0.40 | 0.10 | 0.10 | 0.10 | 0.10 | 0.10 | 0.05 |
|  | {(A) + (B)}/(C) | 0.0385 | 0.1538 | 0.3077 | 0.0769 | 0.0769 | 0.0769 | 0.0769 | 0.0769 | 0.0385 |
|  | Biofilm-dispersing effect | 65.0% | 49.7% | 66.3% | 55.0% | 50.0% | 52.0% | 45.0% | 50.0% | 40.5% |
|  | Bactericidal effect | 7.40% | 7.66% | 7.30% | 8.9% | 8.1% | 9.7% | 10.43% | 13.16% | 8.35% |

*[1]Amisoft MS-11 (Ajinomoto Co., Ltd.)

*[2]Amisoft LS-11 (Ajinomoto Co., Ltd.)

TABLE 2

|  | Example 7 | Example 8 | Example 9 | Comparative Example 4 | Comparative Example 5 | Comparative Example 6 |
|---|---|---|---|---|---|---|
| (A) Sodium myristoyl glutamate[*1] | 0.05 | 0.075 | 0.025 | 0.1 | 0 | 0 |
| (B) Sodium lauroyl glutamate[*2] | 0.05 | 0.025 | 0.075 | 0 | 0.1 | 0 |
| (C) Sodium lauryl sulfate | 1.3 | 1.3 | 1.3 | 1.3 | 1.3 | 1.3 |
| (D) Purified water | 98.6 | 98.6 | 98.6 | 98.6 | 98.6 | 98.7 |
| Total | 100 | 100 | 100 | 100 | 100 | 100 |
| (A)/(B) | 1.00 | 3.00 | 0.33 | — | 0.00 | — |
| (A) + (B) | 0.10 | 0.10 | 0.10 | 0.10 | 0.10 | 0.00 |
| {(A) + (B)}/(C) | 0.0769 | 0.0769 | 0.0769 | 0.0769 | 0.0769 | 0.0000 |
| Foaming stability and persistence | 0.024 | 0.020 | 0.000 | 0.091 | 0.183 | 0.290 |

[*1-2]The same as Table 1

Examples 10 and 11 and Comparative Examples 7 to 9

Each dentifrice composition was prepared according to the formulations shown in Table 3 by feeding purified water warmed to 60° C. to 80° C. in advance into a thermostat and then ingredients (A), (B), and (C) and other ingredients, and mixing them.

The biofilm-dispersing effect and bactericidal effect of the resulting dentifrice compositions were evaluated according to the following methods, and the foaming stability and persistence were evaluated by the same method as above.

Regarding the evaluation of foaming stability and persistence, when the value of rate of change in the height of foam, (Δfoam), determined by the above-mentioned formula was within a range of from −0.15 to 0.15, it was judged that moderate foaming was provided without excessive foaming and was excellent in stability and persistence.

The results are shown in Table 3.

<<Biofilm-Dispersing Effect>>

The biofilm-dispersing effect was evaluated as in the liquid oral composition except that in "2) Evaluation of biofilm-dispersing effect" in <<Biofilm-dispersing effect>> of the liquid oral composition, 1 mL of the 4-fold diluted solution was added.

<<Bactericidal Effect>>

The bactericidal effect was evaluated as in the liquid oral composition except that in "2) Evaluation of bactericidal effect" in <<Bactericidal effect>> of the liquid oral composition, 1 mL of the 4-fold diluted solution was added.

TABLE 3

|  |  | Example 10 | Example 11 | Comparative Example 7 | Comparative Example 8 | Comparative Example 9 |
|---|---|---|---|---|---|---|
| (A) | Sodium myristoyl glutamate[*1] | 0.025 | 0.05 | 0.025 | 0 | 0.025 |
| (B) | Sodium lauroyl glutamate[*2] | 0.025 | 0.05 | 0 | 0.025 | 0.025 |
| (C) | Sodium lauryl sulfate | 1.3 | 1.3 | 1.3 | 1.3 | 1.3 |
|  | Sodium fluoride | 0.21 | 0.21 | 0.21 | 0.21 | 0.21 |
| (E) | Cetylpyridinium chloride | 0.02 | 0.02 | 0.02 | 0.02 | 0.02 |
| (F) | Erythritol | 41 | 41 | 41 | 41 | 41 |
|  | Sorbitol (70%) | 29.945 | 29.945 | 29.945 | 29.945 | 29.945 |
|  | Glycerol | 4.5 | 4.5 | 4.5 | 4.5 | 4.5 |
|  | Polyethylene glycol 600 | 3.5 | 3.5 | 3.5 | 3.5 | 3.5 |
|  | Silicic anhydride A[*3] | 6 | 6 | 6 | 6 | 6 |
|  | Silicic anhydride B[*4] | 5 | 5 | 5 | 5 | 5 |
|  | Sodium carboxymethyl cellulose X[*5] | 0.05 | 0.05 | 0.05 | 0.05 | 0.05 |
|  | Sodium carboxymethyl cellulose Y[*6] | 0.19 | 0.19 | 0.19 | 0.19 | 0.19 |
|  | Carrageenan | 0.065 | 0.065 | 0.065 | 0.065 | 0.065 |
|  | Polyoxyethylene sorbitan stearate | 0.1 | 0.1 | 0.1 | 0.1 | 0.1 |
|  | Flavoring agent | 1.2 | 1.2 | 1.2 | 1.2 | 1.2 |
|  | Titanium oxide | 0.3 | 0.3 | 0.3 | 0.3 | 0.3 |
|  | Sodium lauroyl sarcosinate | 0 | 0 | 0 | 0 | 0 |
|  | Sodium saccharide | 0.03 | 0.03 | 0.03 | 0.03 | 0.03 |
|  | Sucralose | 0.03 | 0.03 | 0.03 | 0.03 | 0.03 |
|  | Sodium pyrophosphate, anhydrous | 0 | 0 | 0 | 0 | 0.02 |
|  | Sodium hydroxide solution | 0.01 | 0.01 | 0.01 | 0.01 | 0.01 |
|  | Purified water | 7.9 | 7.9 | 7.9 | 7.9 | 7.8 |
|  | Total | 100 | 100 | 100 | 100 | 100 |
| (D) | Total amount of water | 16.8335 | 16.8335 | 16.8335 | 16.8335 | 16.8135 |
|  | (A)/(B) | 1.00 | 1.00 | — | 0.00 | 1.00 |
|  | (A) + (B) | 0.05 | 0.10 | 0.03 | 0.03 | 0.05 |
|  | Biofilm-dispersing effect | 36.4% | 50.4% | 23.7% | 17.9% | 23.5% |

TABLE 3-continued

|  | Example 10 | Example 11 | Comparative Example 7 | Comparative Example 8 | Comparative Example 9 |
|---|---|---|---|---|---|
| Bactericidal effect | 29.2% | 29.8% | 26.8% | 31.6% | 30.6% |
| Foaming stability and persistence | 0.12 | 0.14 | 0.34 | 0.21 | 0.16 |

*[1-2] The same as Table 1
*[3] Sorbosil AC77 (manufactured by Ineos Silicas Ltd.)
*[4] Sylopure 25 (manufactured by Fuji Silysia Chemical Ltd.)
*[5] Sunrose F35SH (Nippon Paper Industries Co., Ltd.)
*[6] Sunrose F03HC (Nippon Paper Industries Co., Ltd.)

Examples 12 and 13 and Comparative Examples 10 and 11

Each liquid oral composition was prepared according to the formulations shown in Table 4. The biofilm-dispersing effect and bactericidal effect of the resulting liquid oral compositions were evaluated as in Example 1.

The results are shown in Table 4.

TABLE 4

|  |  | Example 12 | Comparative Example 10 | Example 13 | Comparative Example 11 |
|---|---|---|---|---|---|
| (A) | Sodium myristoyl glutamate*[1] | 0.25 | 0 | 0.125 | 0.25 |
| (B) | Sodium lauroyl glutamate*[2] | 0.25 | 0.25 | 0.125 | 0 |
| (C) | Sodium lauryl sulfate | 1.3 | 1.3 | 1.3 | 1.3 |
|  | Sodium fluoride | 0 | 0 | 0 | 0 |
| (E) | Cetylpyridinium chloride | 0 | 0 | 0 | 0 |
|  | Dipotassium glycyrrhizinate | 0 | 0 | 0 | 0 |
| (F) | Erythritol | 0 | 0 | 0 | 0 |
|  | Sodium pyrophosphate, anhydrous | 0 | 0 | 0 | 0 |
| (D) | Purified water | 98.2 | 98.45 | 98.45 | 98.45 |
|  | Total | 100 | 100 | 100 | 100 |
|  | (A)/(B) | 1.00 | 0.00 | 1.00 | — |
|  | (A) + (B) | 0.50 | 0.25 | 0.25 | 0.25 |
|  | {(A) + (B)}/(C) | 0.3846 | 0.1923 | 0.1923 | 0.1923 |
|  | Biofilm-dispersing effect | 28.1% | 7.8% | 48.9% | 24.0% |
|  | Bactericidal effect | 21.1% | 22.8% | 22.0% | 22.5% |

*[1] Amisoft MS-11 (Ajinomoto Co., Ltd.)
*[2] Amisoft LS-11 (Ajinomoto Co., Ltd.)

The invention claimed is:

1. An oral composition comprising the following ingredients (A), (B), (C), and (D):
   (A) from 0.01 mass % to 0 0.27 mass % of sodium myristoyl glutamate;
   (B) from 0.01 mass % to 0 0.27 mass % of sodium lauroyl glutamate;
   (C) from 0.05 mass % to 2 mass % of sodium lauryl sulfate; and
   (D) water
   wherein a mass ratio of the content of the ingredient (A) to the content of the ingredient (B), ((A)/(B)), is from 0.25 to 4; and
   a content of a polyphosphoric acid or a salt thereof is 0.001 mass % or less.

2. The oral composition according to claim 1, further comprising (E) a cationic bactericide.

3. The oral composition according to claim 1, further comprising (F) erythritol.

4. The oral composition according to claim 1, wherein a mass ratio of the total content of the ingredients (A) and (B) to a content of the ingredient (C), ({(A)+(B)}/(C)), is from 0.005 to 4.

5. The oral composition according to claim 1, wherein the total content of the ingredients (A) and (B) is from 0.02 mass % to 0.5 mass %.

6. The oral composition according to claim 3, wherein a content of the ingredient (F) is from 1 mass % to 60 mass %.

7. The oral composition according to claim 1, wherein the oral composition is a dentifrice composition and a content of the ingredient (D) is from 5 mass % to 50 mass %.

8. The oral composition according to claim 7, wherein a mass ratio of the content of the ingredient (A) to the content of the ingredient (D), (A)/(D), is from 0.0005 to 0.01 and a mass ratio of the content of the ingredient (B) to the content of the ingredient (D), (B)/(D), is from 0.0005 to 0.01.

9. The oral composition according to claim 7, further comprising from 5 mass % to 60 mass % of (F) erythritol.

10. The oral composition according to claim 7, wherein the viscosity at 20° C. is from 500 to 10000 dPa·s.

11. The oral composition according to claim 1, wherein the oral composition is a liquid oral composition and a content of the ingredient (D) is 70 mass % or more.

12. The oral composition according to claim 11, wherein a mass ratio of the content of ingredient (A) to the content of ingredient (D), (A)/(D), is from 0.0001 to 0.01 and a mass ratio of the content of ingredient (B) to the content of ingredient (D), (B)/(D), is from 0.0001 to 0.01.

13. The oral composition according to claim 11, further comprising from 1 mass % to 60 mass % of (F) erythritol.

14. The oral composition according to claim 2, wherein the ingredient (E) is at least one selected from the group consisting of a quaternary ammonium compound and biguanide compound.

15. The oral composition according to claim 2, wherein a mass ratio of the content of the ingredient (A) to the content of the ingredient (E), (A)/(E), is from 0.1 to 30.

16. The oral composition according to claim 2, wherein a mass ratio of the total content of the ingredient (A) and the ingredient (B) to the content of the ingredient (E), {(A)+(B)/(E)} is from 0.5 to 80.

17. The oral composition according to claim 1, wherein the oral composition is toothpaste, powder dentifrice, mouthwash, or liquid dentifrice.

* * * * *